United States Patent
Roberts et al.

(10) Patent No.: US 6,582,634 B2
(45) Date of Patent: *Jun. 24, 2003

(54) PROCESS OF MAKING A YARN

(75) Inventors: Ian Roberts, Pencaitland (GB); David McKenzie Hill, Berwick (GB)

(73) Assignee: Peri-Dent Limited, Selkirkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/863,548

(22) Filed: May 22, 2001

(65) Prior Publication Data

US 2001/0041262 A1 Nov. 15, 2001

Related U.S. Application Data (63) Continuation of application No. 09/368,664, filed on Aug. 5, 1999, now abandoned, which is a continuation-in-part of application No. 09/330,491, filed on Jun. 11, 1999, now Pat. No. 6,303,063.

(30) Foreign Application Priority Data

Aug. 6, 1998 (GB) .............................................. 9817011

(51) Int. Cl.$^7$ ......................... A61C 15/04; D01D 5/088; D01D 5/16; D01D 10/02; D01F 1/10
(52) U.S. Cl. ................ 264/103; 264/178 F; 264/210.6; 264/210.7; 264/210.8; 264/211.12; 264/211.14; 264/211.17
(58) Field of Search .............................. 264/103, 178 F, 264/210.6, 210.7, 210.8, 211.12, 211.14, 211.17

(56) References Cited

U.S. PATENT DOCUMENTS 3,800,812 A  4/1974  Jaffe
5,518,670 A  5/1996  Budenbender et al.

FOREIGN PATENT DOCUMENTS

| DE | 35 39 185 A1 | 6/1986 |
| EP | 0 339 935 A2 | 11/1989 |
| FR | 2 095 010 A | 2/1972 |
| GB | 2 128 133 A | 4/1984 |
| GB | 2258 402 A | 2/1993 |
| WO | WO 95 12698 A1 | 5/1995 |
| WO | WO 98 50607 A1 | 11/1998 |

*Primary Examiner*—Leo B. Tentoni
(74) *Attorney, Agent, or Firm*—Adams Evans P.A.

(57) ABSTRACT

A method of converting a plastics material into a yarn, in which the plastics material includes one or more polymers selected from the group consisting of nylon, polyesters, polyethylene, polyvinyl chloride, polyphenylene sulphide, polystyrene. The method includes heating the material to melt it, pumping the melted material through an extruder to form an extruded filament, and cooling the extruded filament. The cooled filament is passed through a first draw roller assembly while elevating the temperature of the filament. The filament is then heated in a heating zone as it exits the first draw roller assembly and, thereafter, the filament is passed through a second draw roller assembly operating at a different linear speed to the first draw roller assembly. The filament is spooled after exiting the second draw roller assembly.

16 Claims, 3 Drawing Sheets

PROCESS OF MAKING A YARN

This application is a continuation of U.S. patent application Ser. No. 09/368,664 filed on Aug. 5, 1999, now abandoned, which is a continuation-in-part of U.S. patent application Ser. No. 09/330,491, filed on Jun. 11, 1999, now U.S. Pat. No. 6,303,063. This application claims the priority of United Kingdom Patent Application No. 9817011.1 on Aug. 6, 1998.

TECHNICAL FIELD AND BACKGROUND OF THE INVENTION

The present invention concerns an improved method for making a plastics material yarn, particularly, but not exclusively, a dental floss.

Methods and materials used for the manufacture of dental floss are known to give reasonable results. However, there is a desire to improve the methods for manufacturing the floss and to find materials that will provide the desired properties in the floss.

SUMMARY OF THE INVENTION

According to one aspect of this invention there is provided a method of converting a plastics material into a yarn, comprising heating the plastics material to melt it, passing melted material through an extrusion die to form an extruded filament, and thereafter cooling the filament, wherein the plastics material is selected from the group comprising nylon, polyesters, polyethylene, polyvinyl chloride, polyphenylene sulphite, polystyrene.

The method may further include the step of passing the extruded filament through a draw roller assembly while elevating the temperature of the filament. The filament may be heated after exiting from the draw roller assembly.

The method may further include the step of passing the extruded filament through a plurality of draw roller assemblies whereby the temperature of the filament is elevated at least one of the assemblies. The filament may be heated after exiting from at least one of the draw roller assemblies.

According to another aspect of the present invention there is provided a method of converting a plastics material into a yarn the plastics material being selected from the group comprising nylon, polyesters, polyethylene, polyvinyl chloride, polyphenylene sulphide, polystyrene, the method comprising heating the material to melt it, pumping melted material through an extrusion die to form an extruded filament, cooling the extruded filament, passing the extruded filament through a first draw roller assembly while elevating the temperature of the filament, heating the filament in a heating zone as it exits from the first draw roller assembly and, thereafter, passing the filament through a second draw roller assembly operating at a different linear speed than the first draw roller assembly and spooling the filament exiting the second draw roller assembly.

Means may be included for pumping the material through the extrusion die. The pumping means may be a metering pump which may operate in the region of substantially 3 to substantially 18 rpm. preferably substantially 3 to substantially 5 rpm. In one embodiment, the metering pump may operate at substantial 7 to substantially 6 rpm. In another embodiment, the pump may operate at substantially 7 rpm. In a third embodiment the pump may operate at substantially 5 to substantially 4 rpm.

The plastics material may include Silica. Preferably, the silica is added in the form of particles. Preferably, silica is added to the material in an amount of 0 to substantially 25% wt/wt, suitably substantially 1 to substantially 5%. The silica may be added to the material prior to or during heating thereof. The silica may be a coloured silica.

The plastics material may include a silicone. The silicone may be linear polydimethyl silicone, suitably one sold by Dow Corning under the designation MB50-001 SILICONE MASTERBATCH. The silicone may be added in an amount 0 to substantially 50% wt/wt, preferably 0 to substantially 25% wt/wt, more preferably substantially 10 to substantially 15% wt/wt.

The material may further include polytetrafluroethylene (PTFE), for example, in an amount of substantially 5 to substantially 10% wt/wt.

The material may include a rubberising agent. The agent may be, for example a product sold under the trade mark ADFLEX. Alternatively, the agent may be any other similar product. The rubberising agent may be added to the material in an amount 0 to substantially 70% wt/wt, preferably 0 to substantially 40% wt/wt. The use of the rubberising agent has the effect of rendering to the gain a more rubbery texture, which can be advantageous when the yarn is to be used as a dental floss.

In the first embodiment, the rollers in the first heated draw roller assembly are rotating such as to impart to the filament a speed which may lie within the range 0 to substantially 200 m per minute, preferably within the range substantially 10 to substantially 50 m per minute. More preferably it is substantially 20 m per minute.

The temperature of the rollers in the first heated draw roller assembly of the first embodiment may lie within the range 0 to substantially 200° C., preferably within the range substantially 80 to substantially 160° C. More preferably it is substantially 105° C. The temperature in the heating zone at the exit from the first draw roller assembly may lie within the range 0 to substantially 200° C., preferably within the range substantially 80 to substantially 140° C. More preferably it is substantially 120° C.

Preferably the second draw roller assembly operates at a higher speed than the first draw roller assembly. In a first embodiment of the invention the second draw roller assembly is heated.

The temperature of the rollers in the second heated draw roller assembly of the first embodiment may lie within the range 0 to substantially 200° C., preferably within the range substantially 60 to substantially 90° C. More preferably it is substantially 70° C.

The rollers of the second heated draw roller assembly of the first embodiment are rotating such as to impart to the filament a speed which may lie within the range 0 to 1000 m per minute, preferably with the range substantially 50 to substantially 250 m per minute. More preferably it is substantially 95 to substantially 100 m per minute.

In a second embodiment, the filament may be passed through an intermediate draw roller assembly arranged downstream of the first draw roller assembly and upstream of the second draw roller assembly.

In the second embodiment, the extruded filament may, be further heated in a second heating zone as the filament exits the intermediate draw roller assembly.

In the second embodiment, the rollers in the first draw roller assembly are rotating such as to impart to the filament a speed which may lie within the range of substantially 5 to substantially 50 m per minute, conveniently substantially 20 m per minute.

Preferably, the first draw roller assembly of the second embodiment comprises a plurality of rollers, conveniently five. The temperature of at least one of the rollers in the fire draw roller assembly of the second embodiment may lie in the range of substantially 50 to substantially 130° C., conveniently 95 to substantially 110° C., preferably substantially 105° C. Conveniently the roller of the first draw roller assembly arranged furthest downstream thereof is heated. Preferably, the roller immediately upstream of said furthest downstream roller is also heated.

The temperature of the first mentioned heating zone at the exit from the first draw roller assembly of the second embodiment may lie in the range of substantially 50 to substantially 180° C., conveniently substantially 115 to substantially 175° C., preferably substantially 120° C.

The temperature of the second heating zone at the exit from the intermediate draw roller assembly may lie in the range of substantially 50 to substantially 180° C., suitably, substantially 100 to substantially 150° C. conveniently substantially 140° C.

The intermediate draw roller assembly may comprise a plurality of rollers, conveniently five. The rollers in the intermediate draw roller assembly are rotating such as to impart to the filament a speed which may lie in the range substantially 5 to substantially 250 m per minute, conveniently substantially 70 to substantially 175 m per minute, preferably substantially 70 or substantially 75 m per minute. Preferably, the temperature of at least one of the rollers of the intermediate draw roller assembly lies in the range of substantially 50 to substantially 150° C., conveniently substantially 75 to substantially 125° C., preferably substantially 100° C.

The second draw roller assembly in the second embodiment may comprise a plurality of rollers, conveniently five. The rollers in the second draw roller assembly are rotating such as to impart to the filament a speed which may lie in the range substantially 50 to substantially 150 m per minute, conveniently substantially 95 to substantially 100 m or substantially 160 m per minute, preferably substantially 95 or substantially 100 m per minute.

The extruded filament may be cooled as it passes through the second draw roller assembly of the second embodiment. At least one of the rollers of the second draw roller assembly is at a temperature in the range substantially 50 to substantially 100° C., conveniently substantially 60 to substantially 80° C., preferably substantially 70° C. Conveniently, the roller of the second draw roller assembly arranged furthest downstream thereof is cooled. Preferably, the roller immediately upstream of said furthest downstream roller is also cooled.

In one embodiment, flattening means is provided to flatten the filament. The flattening means may comprise at least one roller, and preferably a pair of flattening rollers between which the filament can pass. The flattening rollers are conveniently arranged to impart to the filament a thickness in the region of substantially 0.03 to substantially 0.15 mm, preferably substantially 0.05 to substantially 0.075 mm. Prior to passing through the flattening means the filament may have a thickness of substantially 0.095 mm. The flattening means preferably operates at a pressure in the range of 0 to substantially 200 psi.

Preferably, the flattening means acts to bilaterally orient the molecules in the filament, thereby providing improved lateral strength.

Preferably the filament is extruded in a generally downward direction from the extruder.

Preferably the extruded filament is cooled in a water bath. Preferably the temperature of the water in the bath is controlled.

Preferably the height of the water bath is adjustable to regulate the cross-section of the extruded filament.

Preferably the filament, as it leaves the extruder, takes the form of the extruding die which is generally rectangular in shape having radiused corners.

Preferably the dimensions of the extruder die are substantially 3 mm to substantially 15 m×substantially 0.25 mm to substantially 0.75 mm, more preferably substantially 12 mm×substantially 0.5 mm.

The flow rate of melted granules through the extruder may lie within the range substantially 2 to substantially 12 g per min.

The temperature of the melted granules may lie in the range substantially 200 to substantially 350° C., preferably within the range substantially 250 to substantially 300° C., more preferably substantially 280° C.

Preferably the extruder pressure lies within the range substantially 600 to substantially 1400 psi. Preferably it is substantially 1000 psi. Preferably the speed of the metering pump feeding the molten granules to the extrusion die is substantially 1 to substantially 18 revs per minute, preferably substantially 2 to substantially 8 revs per minute. More preferably it is in the region of substantially 3 to substantially 5 revs per minute.

The water temperature within the cooling bath may be substantially 5 to substantially 50° C., preferably substantially 10 to substantially 40° C. More preferably it is substantially 35° C.

The distance between the exit from the extrusion die and the water level in the cooling bath may lie within the range substantially 2 to substantially 40 mm, preferably substantially 2 to substantially 15 mm. In one embodiment, the distance is substantially 10 mm. More preferably it is in the range of substantially 5 to substantially 10 mm.

The depth of the water within the cooling bath may lie within the range substantially 0.1 to substantially 50 cm, preferably within the range substantially 10 to substantially 20 cm. More preferably it is substantially 15 cm.

The speed of the spooling assembly may lie within the range 0 to substantially 1000 m per minute, preferably within the range substantially 50 to substantially 250 m per minute. More preferably it is substantially 80 m per minute.

Where the material is a polyester, it may be polybutylene terephthalate.

According to another aspect of the present invention there is provided a yarn manufactured in accordance with the method described above.

In a first embodiment, the plastics material yarn may be manufactured by a method comprising heating to a temperature within the range substantially 200 to substantially 300° C. granules of a plastics material, causing the melted granules to flow to an extrusion metering pump at a rate lying within the range substantially 2 to substantially 12 g per min, passing the melted material through the extrusion metering pump operating it at a speed within the range substantially 1 to substantially 18 revs per minute to create an extrusion pressure lying within the range substantially 600 to substantially 1400 psi, extruding the material through a die and guiding the extruded filament into a bath located between substantially 2 and substantially 40 mm below the exit from the extruder die and containing a cooling fluid, for example water, at a temperature lying within the range substantially 5 to substantially 50° C., passing extruded filament from the water bath to a first heated draw roller assembly where the rollers are heated to a temperature of between 0 to substantially 200° C. and pass filament therethrough at a speed lying within the range 0 to substantially 200 m per minute, heating the filament exiting from the first draw roller assembly in a heating zone to a temperature lying within the range 0 to substantially 200° C. passing the material through a second heated draw roller assembly where the rollers are heated to a temperature of between 0 to substantially 200° C. and passing the yarn therethrough at a speed of between 0 to substantially 1000 m per minute and spooling filament exiting from the second heated draw roller assembly at a speed of between 0 to substantially 1000 m per minute.

In a second embodiment, the plastics material yarn may be manufactured by a method comprising heating to a temperature within the range of substantially 200 to substantially 300° C. granules of a plastics material, causing the melted granules to flow to an extrusion metering pump, passing the melted material through the pump and extruding the material through a die into a bath located between substantially 2 and substantially 40 mm below the exit of the extruder die and containing a cooling fluid, for example water at a temperature lying within the range of substantially 5 to substantially 50° C., passing the extruded filament from the bath to a first heated draw roller assembly where at least one of the rollers are heated to a temperature lying in the range of substantially 50 to substantially 100° C., and passing the filament therethrough at a speed lying within the range of substantially 15 to substantially 50 m per minute, heating the filament exiting from the first draw roller assembly in a first heating zone to a temperature lying in the range of substantially 100 to substantially 135° C., passing the filament through an intermediate draw roller assembly at a speed lying within the range of substantially 150 to substantially 150 m per minute, heating the filament exiting from the intermediate draw roller assembly in a second heating zone to a temperature lying in the range of substantially 100 to substantially 150° C., passing the filament through a second draw roller assembly where at least one of the rollers is cooled to a temperature lying in the range of substantially 50 to substantially 100° C., and spooling the filament exiting from the second draw roller assembly.

According to another aspect of the invention there is provided a plastics material yarn having a width in the range of substantially 0.5 to substantially 4 mm, and a decitex in the range of substantially 400 to substantially 1500, wherein the plastics material is selected from the group comprising nylon, polyesters, polyethylene, polyvinyl chloride, polyphenylene sulphide, polystyrene.

Preferably, the width of the yarn is in the range of substantially 0.5 to substantially 2 mm. The thickness of the yarn may be in the range of substantially 0.03 to substantially 0.15 mm.

Preferably, the tensile strength of the yarn is in the range of substantially 12 to substantially 50N., more preferably substantially 15 to substantially 30N. The width of the yarn may be in the range of substantially 0.5 to substantially 2 mm, suitably substantially 0.6 to substantially 1.5 m. The decitex of the yarn may be in the range of substantially 550 to substantially 1000.

The plastics material may include a silicone. The silicone may be linear polydimethyl silicone, suitably one sold by Dow Corning under the designation MB50-001 SILICONE MASTERBATCH. The silicone may be added in an amount 0 to substantially 50% wt/wt, preferably 0 to substantially 25% wt/wt, more preferably substantially 10 to substantially 15% wt/wt.

The material may include PTFE, for example in an amount of substantially 5 to substantially 10% wt/wt.

The material may include silica, which may be in the form of particles. Preferably, the silica comprises substantially 1 to substantially 5% wt/wt of the material. The silica may be a coloured silica.

The material may include a rubberising agent. The agent may be, for example a product sold under the trade mark ADFLEX. Alternatively, the agent may be any other similar product. The rubberising agent may be added to the material in an amount 0 to substantially 70% wt/wt, preferably 0 to substantially 40% wt/wt. The use of the rubberising agent has the effect of rendering to the gain a more rubbery texture, which can be advantageous when the yarn is to be used as a dental floss.

The material may include a colouring, for example Titanium dioxde. The material may include from 0 to substantially 55wt/wt of said colouring, preferably substantially 1% wt/wt.

Where the material is polyester, it may comprise polybutylene terephthalate.

According to another aspect of this invention there is provided apparatus for converting a plastics material into a yarn, the apparatus comprising means for melting the material, means for pumping melted material through an extrusion die to form an extruded filament, means for cooling the extruded filament, a first draw roller assembly to draw the extruded filament therethrough, heating means to heat at least one of the rollers of said first draw roller assembly, a heating zone arranged at the exit of the first draw roller assembly to heat the extruded filament exiting from said first draw roller assembly, a second draw roller assembly operating at a different linear speed to the first draw roller assembly, and spooling means for spooling the filament exiting from the second draw roller assembly.

In a first embodiment, the rollers in the first heated draw roller assembly are rotating such as to impart to the filament a speed which may lie within the range 0 to substantially 200 m per minute, preferably within the range substantially 10 to substantially 50 m per minute. More preferably it is substantially 20 m per minute.

The temperature of the rollers in the first heated draw roller assembly of the first embodiment may lie within the range 0 to substantially 200° C., preferably within the range substantially 80 to substantially 160° C. More preferably it is substantially 105° C. The temperature in the heating zone at the exit from the first draw roller assembly may lie within the range 0 to substantially 200° C., preferably within the range substantially 80 to substantially 140° C. More preferably it is substantially 120° C.

Preferably the second draw roller assembly operates at a higher speed than the first draw roller assembly. In the first embodiment of the invention the second draw roller assembly may be heated.

The temperature of the rollers in the second heated draw roller assembly of the first embodiment may lie within the range 0 to substantially 200° C., preferably within the range substantially 60 to substantially 90° C. More preferably it is substantially 70° C.

The rollers of the second heated draw roller assembly of the first embodiment are rotating such as to impart to the filament a speed which may lie within the range 0 to substantially 1000 m per minute, preferably within the range substantially 50 to substantially 250 m per minute. More preferably it is substantially 95 to substantially 100 m per minute.

In a second embodiment, the apparatus may include an intermediate draw roller assembly arranged downstream of the first draw roller assembly and upstream of the second draw roller assembly.

In the second embodiment the apparatus may include a second heating zone to heat the filament, the second heating zone being arranged at the exit of the intermediate draw roller assembly. Conveniently, intermediate draw roller assembly is substantially unheated. The temperature at the second heating zone is preferably in the range of substantially 50 to substantially 180° C.

In the second embodiment, the rollers in the first draw roller assembly are rotating such as to impart to the filament a speed which may lie within the range of substantially 15 to substantially 50 m per minute, conveniently substantially 20 m per minute.

Preferably, the first draw roller assembly of the second embodiment comprises a plurality of rollers, conveniently five. The temperature of at least one of the rollers in the first draw roller assembly of the second embodiment may lie in the range of substantially 50 to substantially 130° C., conveniently substantially 95 to substantially 110° C. Conveniently the roller of the first draw roller assembly arranged furthest downstream thereof is heated. Preferably, the roller immediately upstream of said furthest downstream roller is also heated.

The temperature of the first mentioned heating zone at the exit from the first draw roller assembly of the second embodiment may lie in the range of substantially 50 to substantially 180° C., conveniently substantially 115 to substantially 175° C., preferably substantially 120° C.

The temperature of the second heating zone at the exit from the intermediate draw roller assembly may lie in the range of substantially 50 to substantially 180° C., suitably substantially 100 to substantially 150° C., conveniently substantially 140° C.

The intermediate draw roller assembly may comprise a plurality of rollers, conveniently five. The rollers in the intermediate draw roller assembly are rotating such as to impart to the filament a speed which may lie in the range substantially 50 to substantially 150 m per minute, conveniently substantially 70 to substantially 175 m per minute, preferably substantially 70 or substantially 75 m per minute. Preferably, the temperature of at least one of the rollers of the intermediate draw roller assembly lies in the range of substantially 50 to substantially 150° C., conveniently substantially 75 to substantially 125° C., preferably substantially 100° C.

The second draw roller assembly in the second embodiment may comprise a plurality of rollers, conveniently five. The rollers in the second draw roller assembly are preferably rotating such as to impart to the filament a speed which may lie in the range substantially 5 to substantially 250 m per minute, suitably substantially 100 to substantially 250 m per minute, conveniently substantially 95 to substantially 100 m per minute, preferably substantially 95 or substantially 100 m per minute.

The second draw roller assembly of the second embodiment may be heated to a temperature below that of the intermediate draw roller assembly. At least one of the rollers of the second draw roller assembly is at a temperature in the range substantially 50 to substantially 100° C., conveniently substantially 60 to substantially 80° C. Preferably substantially 70° C. Conveniently, the roller of the second draw roller assembly arranged furthest downstream thereof is cooled. Preferably, the roller immediately upstream of said furthest downstream roller is also cooled.

In one embodiment, flattening means is provided to flatten the filament. Preferably, the flattening means comprises at least one roller, and preferably a pair of flattening rollers between which the filament can pass. The flattening rollers are conveniently arranged to impart to the filament a thickness in the region of substantially 0.03 to substantially 0.15 mm, preferably substantially 0.05 to substantially 0.075 mm. Prior to passing through the flattening means the filament may have a thickness of substantially 0.095 mm.

Preferably, the flattening means acts to bilaterally orient the molecules in the filament, thereby providing improved lateral strength.

Preferably the filament is extruded in a generally downward direction from the extruder.

Preferably the cooling means is a water bath. Preferably the temperature of the water in the bath is controlled.

Preferably the height of the water bath is adjustable to regulate the cross-section of the extruded filament.

The flow rate of melted granules through the extruder may lie within the range substantially 2 to substantially 12 g per min.

The melting means may be adapted to heat the material to a temperature in the range substantially 200 to substantially 350° C., preferably within the range substantially 250 to substantially 300° C.

Preferably the extruder pressure lies within the range substantially 600 to substantially 1400 psi. Preferably it is substantially 1000 psi. Preferably the speed of the metering pump feeding the molten granules to the extrusion die is 1 to 18 revs per minutes preferably substantially 2 to substantially 8 revs per minute. More preferably it is in the region of substantially 3 to substantially 5 revs per minute.

The water temperature within the cooling bath may be substantially 5 to substantially 500° C., preferably substantially 10 to substantially 40° C. More preferably it is substantially 35° C.

The distance between the exit from the extrusion die and the water level in the cooling bath may lie within the range substantially 2 to substantially 40 mm, preferably substantially 2 to substantially 15 mm. More preferably it is in the range of substantially 5 to substantially 10 mm. In one embodiment, the distance is substantially 10 mm.

When a dental floss has to be formed, the distance between the extrusion die and the water level may lie within the range substantially 2 to substantially 15 mm. More preferably it is substantially 10 mm. The depth of the water within the cooling bath may lie within the range substantially 0.1 to substantially 50 cm, preferably within the range substantially 10 to substantially 20 cm. More preferably it is substantially 15 cm.

The speed of the spooling assembly may lie within the range 0 to substantially 1000 m per minute, preferably within the range substantially 50 to substantially 250 m per minute. More preferably it is substantially 80 m per minute.

BRIEF DESCRIPTION OF THE DRAWINGS

Embodiments of the present invention will now be described by way of example only reference to the accompanying drawings in which.

DESCRIPTION OF THE PREFERRED EMBODIMENT AND BEST MODE

Figure 1:
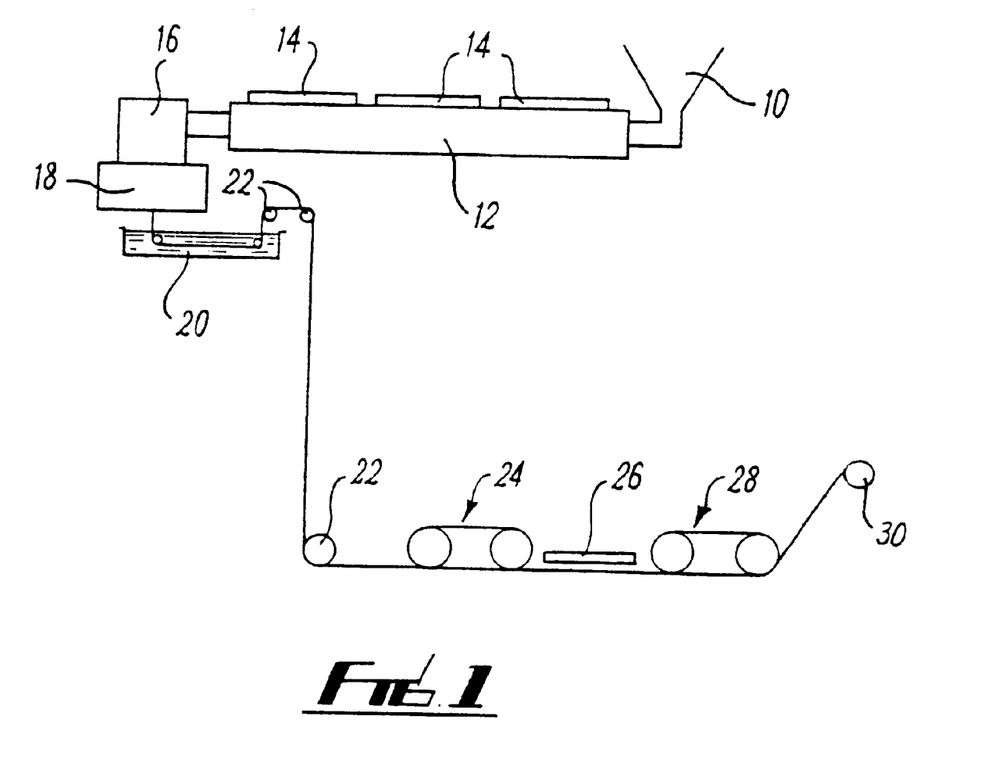
FIG. 1 shows diagrammatically a first embodiment of an apparatus for manufacturing plastics material yarn.

Referring to FIG. 1, there is shown a first embodiment of apparatus for manufacturing plastics material yarn, for example a dental floss or tape. The apparatus comprises a hopper 10 to which nylon granules of the type known as B35, MFF01 are supplied.

Further ingredients can also be added at this stage to form a mixture. One of these further ingredients is polytetrafluoroethylene, which can be added in the form of granules, in an amount of 5 to 10% of the final mixture.

Silica particles can be added to the hopper 10 with the other ingredients. The silica can be added in an amount of 1 to 5% wt/wt. The silica can be coloured to provide the yarn with a mottled appearance. The silica has the effect, when the yarn is used as a dental floss or tape, of an abrasive to enhance the cleaning of the teeth.

A silicone may also be added. A suitable such silicone is one manufactured by Dow Corning under the designation MB50-001 SILICONE MASTERBATCH. The silicone may be added in an amount of 5 to 20% wt/wt. The silicone is provided in the form of pellets or granules. A rubberising agent may also be added, for example a product sold under the trade ark ADFLEX, which may be added in an amount of 0 to 40% wt/wt.

The granules or the mixture are drawn into an extruder barrel 12 provided with heaters 14 and melted material from the extruder barrel 12 passes through a metering pump 16 feeding a diehead 18, the diehead providing an extrusion aperture of generally rectangular form having radius corners, the aperture being 8×0.06 mm with the axis of the extrusion aperture being in a generally vertical direction so that extruded filament leaves the die travelling in a downward direction.

The extruded filament is received in a water-filled cooling bath 20 and after passing therethrough it is guided by guide-rollers 22 into first heated draw roller assembly where the filament is heated and subjected to tension to extend it. Filament exiting from the first draw roller assembly 24 is re-heated under a hotplate 26 before passing into a second heated draw roller assembly where it is subjected to further tension and heat, the finally treated material being spooled on a spooling assembly 30.

With a nylon staring material, known as B35,MFF01 the apparatus described above can be operated under the following ranges of conditions:

| | |
|---|---|
| Resin Melt flow: | 2 to 12 g per minute |
| Melt Temp: | 200 to 300° C. |
| Extrusion Pressure: | 600 to 1400 psi |
| Metering Pump Speed: | 1 to 18 revs per minute |
| Water Bath - Temp: | 5 to 50° C. |
| Die Height Above Water Level: | 2 to 40 mm |
| Water Depth: | 0.1 to 50 cm |
| Roller 1 Speed: | 0 to 200 meters per minute |
| Roller 1 Temp: | 0 to 200° C. |
| Hot Plate: | 0 to 200° C. |
| Roller 2 Speed: | 0 to 1000 meters per minute |
| Roller 2 Temp: | 0 to 200° C. |
| Take Up Speed: | 0 to 1000 meters per minute |

With the above statistics stating material B35, MFF01 at about 99% wt/wt, and $TiO_2$ colourant at 1% wt/wt the apparatus described above results in a yarn having the following properties.

| | |
|---|---|
| Width: | 0.6 mm, 1.1 mm or 1.5 mm (depending upon the distance from the die head to the water bath) |
| Decitex: | 530 to 1000 |
| Tensile strength; | 23 to 45N |

In one specific example, the apparatus is operated under the following conditions.

EXAMPLE 1

| | |
|---|---|
| Resin Melt flow: | MDI = 3.2 |
| Melt Temp: | 280° C. |
| Extrusion Pressure: | 1000 psi |
| Metering Pump Speed: | 5 revs per minute |
| Water Bath - Temp: | 35° C. |
| Die Height Above Water Level: | 10 mm |
| Water Depth: | 15 cm |
| Roller 1 Speed: | 20 meters per minute |
| Roller 1 Temp: | 105° C. |
| Hot Plate: | 120° C. |
| Roller 2 Speed: | 100 meters per minute |
| Roller 2 Temp: | 70° C. |
| Take Up Speed: | 80 meters per minute (1% above roller 2 speed) |

The example described above provide a nylon yarn in tape form which is suitable, if necessary after further treatment, for example, coating with wax with additives therein into a dental interproximal cleaning tape.

If a dental floss is required the same apparatus can be used but the water bath is lowered to a distance of between 4 and 8 mm from the exit from the extruder.

Figure 2:
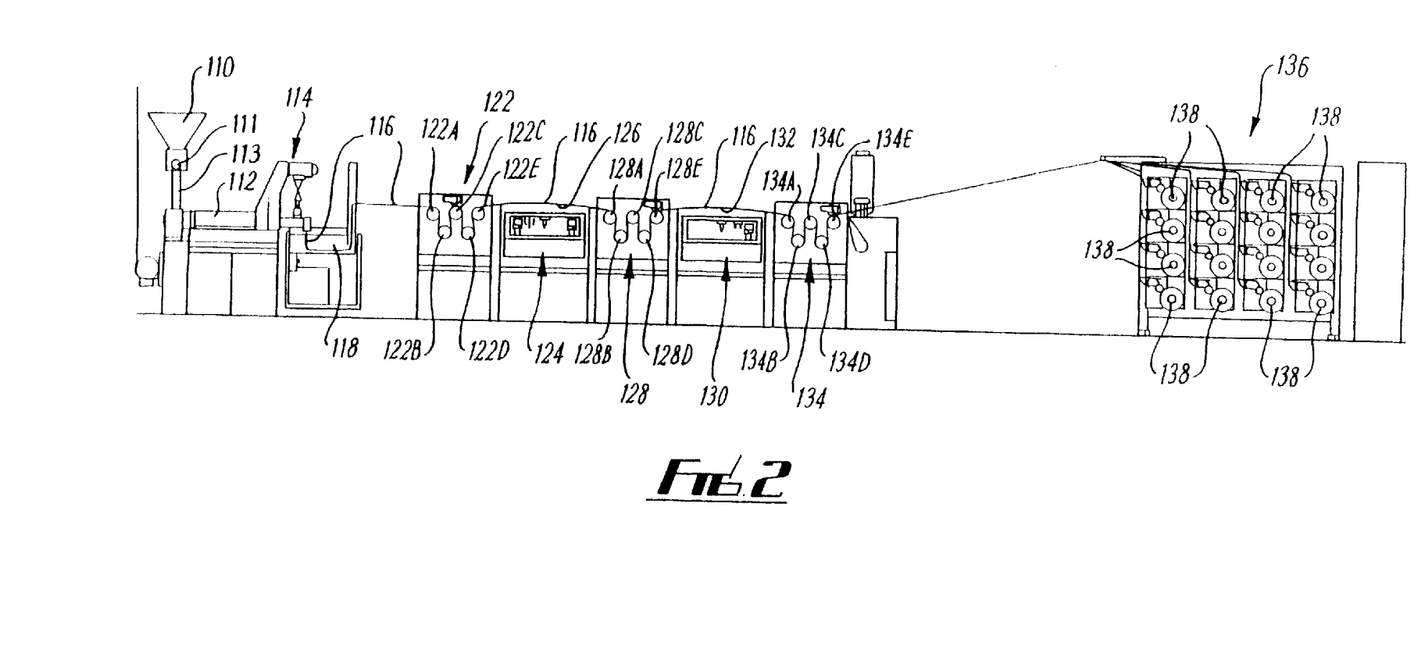
FIG. 2 shows diagrammatically a second embodiment of an apparatus for manufacturing plastics material yarn.

Referring to FIG. 2 there is shown a second embodiment of apparatus for manufacturing plastics material yarn, for example a dental floss. The apparatus 10 comprises one or more feed hoppers 110 to feed one or more ingredients to a screw mixing barrel 112. The ingredients are suitably the same as those described for the first embodiment. If desired a white colouring material e.g. $TiO_2$ can be added in an amount of about 1% wt/wt. A separate hopper 110 is provided for each of the ingredients and the, or each, hopper 110 is provided with a screw feed 111 to feed a predetermined amount of the ingredient to the mixing barrel in at a predetermined rate. Between the hopper(s) 110 and the mixing barrel there is provided a vertical tube 113 known in the art to control the rate of feed of the material to the mixing barrel 12.

The mixing barrel 112 is heated to melt the material therein and the molten material is compressed in the barrel 112. The temperature inside the mixing barrel 112 is at about 280° C. A pump and die head assembly 114 is provided at the exit of the barrel 112 to pump the molten material through dies of appropriate shape to form a plurality of extruded filaments 116.

The filaments 116 are extruded downwardly into a cooling water bath 118 at a temperature of about 12° C. to cool the extruded filaments. The distance between the downwardly facing die apertures and the surface of the water bath determines the width of filament passing through the bath 118.

The filaments 116 then pass over a plurality of guide rollers 120 to a first draw roller assembly 122 comprising five rollers 122A, B, C, D and E. The roller 122E which is furthest downstream of the rollers of the first draw roller assembly 122, and the roller 122D immediately upstream of the roller 122E, are heated to a temperature of about 105° C. The rollers of the first draw roller assembly 122 are rotating such as to impart to the filaments 116 a speed of about 20 m per minute.

A first heating zone 124 is arranged adjacent, and downstream, of the first draw roller assembly 122. The first heating zone 124 comprises an upwardly convex heating plate 126 across which the filaments 116 pass. The heating plate 126 of the first heating zone 124 is heated to a temperature of about 120° C.

Downstream of the first heating zone is an intermediate draw roller assembly 128 comprising five rollers 128A, B, C, D and E. The rollers of the intermediate draw roller assembly 128 are rotating such as to impart to the filaments 116 a speed of about 70 or 75 m per minute. This difference in speed between the rollers of the first draw roller assembly 122 and the rollers of the intermediate draw roller assembly 128 causes the filament 116 to stretch and consequently effects a reduction in the width of the filament 116. The final two downstream rollers 128D and E are heated to a temperature of about 100° C.

A second heating zone 130 is arranged adjacent, and downstream of the intermediate draw roller assembly 128. The second heating zone 130 comprises an upwardly convex heating plate 132 across which the filaments 116 pass. The heating plate 132 is heated to a temperature of about 140° C.

A second draw roller assembly 134 is provided downstream of the second heating zone 130 and adjacent thereto. The second draw roller assembly 134 comprises five rollers 134A to 134E. The roller 134E which is furthest downstream of the rollers of the second draw roller assembly 134, and the roller 134D immediately upstream of the roller 134E, are heated to a temperature of about 70° C. The rollers of the second draw roller assembly 134 are rotating such as to impart to the filaments 116 a speed of about 95 m per minute. The difference in speed between the rollers of the second draw roller assembly 134 and the intermediate draw roller assembly 128 and the passage of the filaments 116 across the heating zone 130 results in the relaxation of the filaments 116 to ensure there is no tension therein.

The cooling of the filaments 116 by the rollers 134D and E results in filaments that can be handled and spooled for storage.

After the second draw roller assembly 134, the filaments 116 pass to spooling means 136, known in the art at which each filament 116 are spooled into a respective individual bobbin 138 for storage.

The apparatus described above with reference to FIG. 2 can be operated under the following ranges of conditions.

| Material | |
| --- | --- |
| Polymer | 10% to 100% |
| ADFLEX | 0% to 70% |
| MASTERBATCH | 0% TO 10% |
| Silica | 0% to 25% |
| Resin melt flow: | 2 to 12 g/min |
| Melt temp: | 150° to 130° C. |
| Extrusions pressure: | 600 to 1400 psi |
| Metering pump speed: | 1 to 18 revs per minute |
| Water bath temp: | 5 to 50° C. |
| Die height above water level: | 2 to 40 mm |

| -continued | |
| --- | --- |
| Material | |
| Water depth: | 0.1 to 50 cm |
| Roller speed: | 5 to 50 meters/minute |
| Roller temp: | 50 to 130° C. |
| Hotplate temp: | 50 to 180° C. |
| Intermediate roller speed: | 5 to 250 meters/minute |
| Hotplate 2 temp: | 50 to 180° C. |
| Roller 2 speed: | 5 to 250 meters/minute |
| Flattening pressure: | 0 to 200 psi |

With the above described starting conditions and material a product would be produced as follows.

| Product Specification | |
| --- | --- |
| Width: | 0.5 to 2 mm |
| Thickness: | 0.03 to 0.15 mm |
| Decitex: | 400 to 1500 |
| Tensile strength: | 12 to 50N |

EXAMPLE 2

With a nylon starting material which comprises 90% wt/wt Nylon (sold under the trade mark Zytel, No. ST 7301 by Du Pont), 1% silicone MASTERBATCH, and 9% silica, the apparatus described above and shown in FIG. 2 can be operated under the following conditions.

| | |
| --- | --- |
| Resin melt flow: | 10 g/min |
| Melt temp: | 265° C. |
| Extrusion pressure: | 1200 psi |
| Metering pump speed: | 5.4 revs per minute |
| Water bath temp: | 25° C. |
| Die height above water level: | 12 mm |
| Water depth | 15 cm |
| Roller speed: | 14 meters/minute |
| Roller temp: | 110° C. |
| Hot plate temp: | 135° C. |
| Intermediate roller speed: | 69.4 meters/minute |
| Flattening pressure: | 40 psi |

With the above starting materials and conditions, a dental floss is produced as follows.

| Product Specification | |
| --- | --- |
| Width: | 1.5 mm |
| Thickness: | 0.05 mm |
| Decitex: | 700 |
| Tensile strength: | 21.5N |

EXAMPLE 4

With a low density polyethylene starting material, which comprises 50% wt/wt for density polyethylene (sold under the designation: Type 1070 MN 18 by Altochem), 40% wt/wt ADFLEX, 1% wt/wt MASTERBATCH, and 9% wt/wt silica, the apparatus described above and shown in FIG. 2 can be operated under the following conditions.

| Resin melt flow | 4 g/min |
|---|---|
| Melt temp: | 230° C. |
| Extrusions pressure | 1200 psi |
| Metering pump speed | 7 rpm |
| Water bath temp: | 25° C. |
| Die height above water level: | 10 mm |
| Water depth: | 15 cm |
| Roller speed: | 10 meters per minute |
| Roller temp: | 100° C. |
| Hotplate temp: | 125° C. |
| Intermediate roller speed: | 80 meters per minute |
| Hotplate 2 speed: | 135° C. |
| Roller 2 speed: | 78.5 meters |
| Flattening pressure: | 100 psi |

With the above starting materials and conditions, a dental floss is produced, as follows.

| Product Specification | |
|---|---|
| Width: | 1.34 mm |
| Thickness: | 0.065 mm |
| Decitex; | 750 |
| Tensile strength: | 14N |

Figure 3:
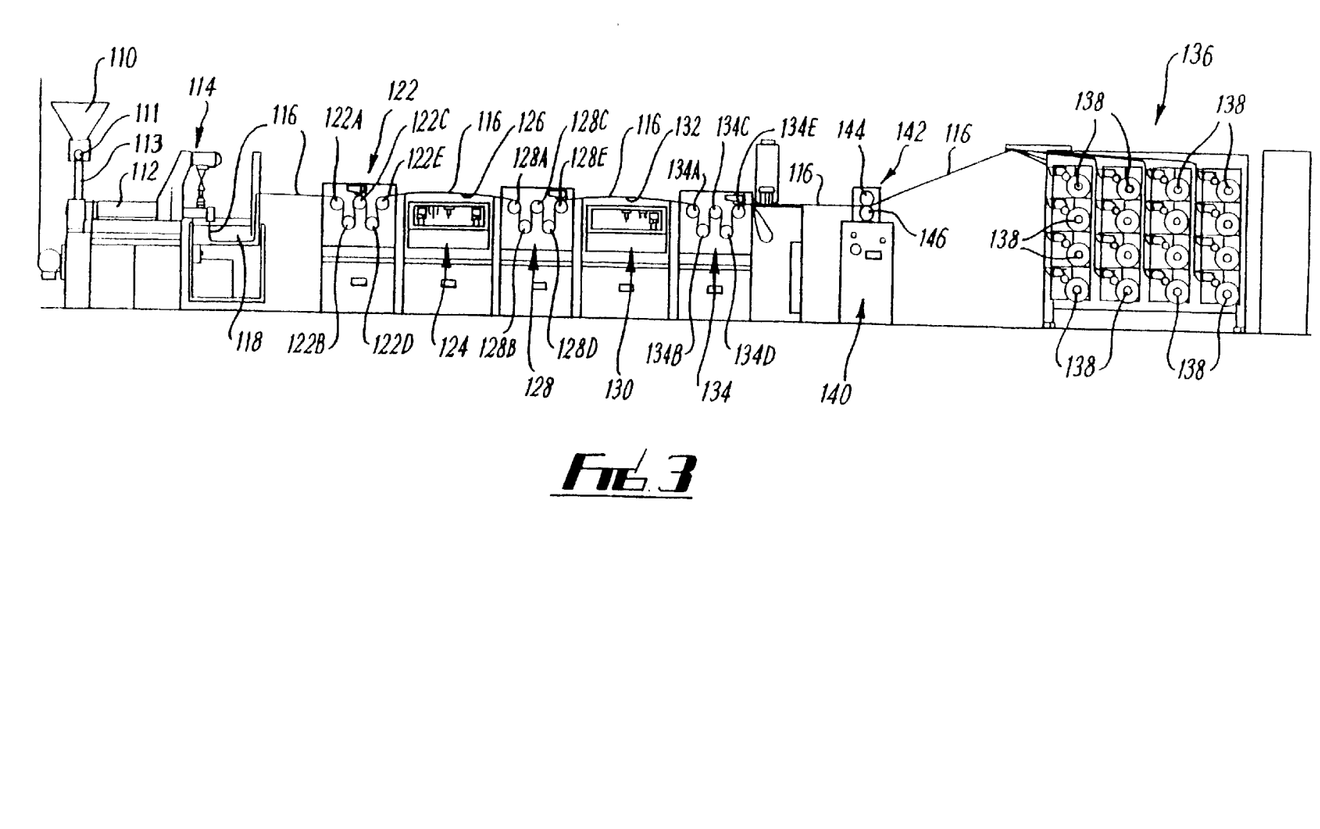
FIG. 3 shows diagrammatically a third embodiment of an apparatus for manufacturing plastics material yarn.

Referring to FIG. 3, there is shown a third embodiment of the apparatus which comprises all the features of the apparatus shown in FIG. 2 and these have been designated with the same reference numerals.

In addition, the apparatus shown in FIG. 3 also includes flattening means 140 comprising a pair 142 of opposed rollers 144, 146, between which the filaments 116 passes. The surfaces of the rollers 144, 146 are spaced from each other at the point at which the filaments 116 passes therebetween by a distance sufficient to flatten the filaments 116 from a thickness of substantially 0.095 mm, to a thickness of between substantially 0.05 mm and substantially 0.075 mm.

The flattening of the filaments 116 by the flattening means 140 bilaterally orient the molecules in the filaments 116 thereby increasing the lateral strength of the filaments 116.

Whilst endeavouring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

What is claimed is:

1. A method of converting a plastics material into a dental floss, the plastics material comprising one or more polymers selected from the group consisting of nylon, polyesters, polyethylene, polyvinyl chloride, polyphenylene sulphide, and polystyrene, the method comprising heating the material to melt it, pumping the melted material through an extruder to form an extruded filament, cooling the extruded filament, passing the extruded filament through a first drawer roller assembly while elevating the temperature of the filament, heating the filament in a heating zone as it exits from the first drawer assembly and, thereafter, passing the filament through a second drawer assembly operating at a different linear speed to the first drawer assembly and spooling the filament exiting the second drawer assembly, wherein the dental floss constitutes the filament and the filament has a width in the range of 0.5 to 4 mm.

2. A method according to claim 1, wherein pumping means comprises a metering pump is provided for pumping the material through the extrusion die, the metering pump operating in the region of substantially 3 to substantially 18 rpm.

3. A method according to claim 1, wherein the plastics material includes one or more components selected from the group consisting of silica, present in the material in an amount of 0 to substantially 25% wt/wt, a silicone, present in the material in an amount 0 to substantially 50% wt/wt, polytetrafluroethylene (PTFE), in an amount of substantially 5 to substantially 10% wt/wt, a rubberising agent, present in the material in an amount 0 to substantially 70% wt/wt.

4. A method according to claim 1, wherein the rollers in the first draw roller assembly are rotating such as to impart to the filament a speed which lies within the range of substantially 5 to substantially 50 m per minute, the temperature of at least one of the rollers in the first draw roller assembly of the second embodiment lying in the range of substantially 50 to substantially 130° C.

5. A method according to claim 1, wherein the temperature of the heating zone at the exit from the first draw roller assembly of the second embodiment lies in the range of substantially 50 to substantially 180° C.

6. A method according to claim 1, wherein the filament is passed through an intermediate draw roller assembly downstream of the first draw roller assembly and upstream of the second draw roller assembly.

7. A method according to claim 6, wherein the filament is further heated in a second heating zone as the filament exits the intermediate draw roller assembly.

8. A method according to claim 7, wherein the temperature of the second heating zone at the exit from the intermediate draw roller assembly lies in the range of substantially 50 to substantially 180° C.

9. A method according to claim 6, wherein the rollers in the intermediate draw roller assembly are rotating such as to impart to the filament a speed in the range substantially 5 to substantially 250 m per minute, and the temperature of at least one of the rollers of the intermediate draw roller assembly lies in the range of substantially 50 to substantially 150° C.

10. A method according to claim 1, wherein the rollers in the second draw roller assembly are rotating such as to impart to the filament a speed which lies in the range substantially 50 to substantially 150 m per minute.

11. A method according to claim 1, wherein the extruded filament is cooled as it passes through the second draw roller assembly of the second embodiment, at least one of the rollers of the second draw roller assembly being at a temperature in the range substantially 50 to substantially 100° C.

12. A method according to claim 1, wherein flattening means is provided downstream of the second draw roller assembly to flatten the filament, the flattening means comprising at least one roller, the flattening rollers being arranged to impart to the filament a thickness in the region of substantially 0.03 to substantially 0.15 mm.

13. A method according to claim 1, wherein the filament is extruded in a generally downward direction from the extruder and is cooled in a water bath after leaving the extruder, the height of the extruder above the water bath being adjustable to regulate the cross-section of the extruded filament.

14. A method according to claim 13, wherein the water temperature within the cooling bath is substantially 5 to substantially 50° C., the distance between the exit from the extrusion die and the water level in the cooling bath may lie within the range substantially 2 to substantially 40 mm, and the depth of the water within the cooling bath lies within the range substantially 0.1 to substantially 50 cm.

15. A method according to claim 13, wherein the flow rate of melted granules through the extruder lies within the range substantially 2 to substantially 12 g per min, the temperature of the melted granules in the extruder lies in the range substantially 200 to substantially 350° C., and the extruder pressure lies within the range substantially 600 to substantially 1400 psi.

16. A method according to claim 1, wherein the spooling of the filament takes place on a spool assembly, the speed of the spooling assembly lying within the range 0 to substantially 1000 m per minute.

* * * * *